United States Patent [19]

Pang et al.

[11] Patent Number: 4,687,840

[45] Date of Patent: Aug. 18, 1987

[54] HYPOTENSIVE ACTIVE PEPTIDES

[75] Inventors: Peter K. T. Pang; Thomas E. Tenner, Jr., both of Lubbock, Tex.

[73] Assignee: Texas Tech University Health Sciences Center, Lubbock, Tex.

[21] Appl. No.: 828,380

[22] Filed: Feb. 11, 1986

[51] Int. Cl.$^4$ .......................... C07K 5/08; C07K 5/06; C07D 207/00
[52] U.S. Cl. .................................. 530/331; 548/533; 548/532
[58] Field of Search ................ 530/330, 331; 548/533, 548/532

[56] References Cited

PUBLICATIONS

Pettit; Synthetic Peptides, vol. 5, (1980) 190–193.
Pettit; Synthetic Peptides, vol. 6, (1982) 210, 211, 246 and 247.
Pettit; Synthetic Peptides, vol. 1, (1971) 152, 153, 208 and 209.

Primary Examiner—Delbert R. Phillips
Attorney, Agent, or Firm—Arnold, White & Durkee

[57] ABSTRACT

The present invention provides a hypotensive composition comprising a peptide having the structure X-Y, Y-X, or a salt thereof, wherein X is proline or proline-proline and Y is arginine, lysine, arginine-arginine, lysine-lysine, arginine-lysine, or lysine-arginine, together with a pharmaceutically suitable diluent.

4 Claims, No Drawings

HYPOTENSIVE ACTIVE PEPTIDES

This is a divisional of co-pending application Ser. No. 635,219 filed July 27, 1984, now U.S. Pat. No. 4,585,757.

BACKGROUND OF THE INVENTION

The present invention relates to short peptides, two to four amino acids in length, to be used as antihypertensive agents.

Hypertension is a serious health problem of epidemic proportions. It is estimated that 20% of the adult population of North America have systemic arterial pressures above the accepted normal range. A few direct causes of hypertension, such as pheochromocytoma and primary hyperaldosteronism, are amenable to direct therapeutic intervention. These instances are not the norm. In general, pharmacologic treatment of hypertension involves treating the symptom. Therapy is directed only to a correction of the abnormal pressure. Yet, it is now clear that such therapy can favorably affect prognosis and thus greatly decrease the risk of death due to cardiovascular disease in the affected person.

Essential, or primary, hypertension is a poorly defined condition that is diagnosed by exclusion. It is not known whether hypertension is a disease per se or simply the upper end of a continuous spectrum of blood pressures in the population. In both normotensive and hypertensive individuals, vascular tone is controlled by sympathetic nerve fibers. Even in normotensive individuals, reduction of the vascular tone can reduce the blood pressure. Thus, abnormal sympathetic nerve function is probably not responsible for the increased peripheral resistance that characterizes primary hypertension.

Pharmacologic therapy of hypertension has generally been directed at promoting salt excretion (diuretics) and decreasing vascular tone by both direct (direct vasodilators) and indirect (adrenegic blocking agents) means. Diuretics are an effective means of reducing overall blood volume and thereby reduce blood pressure, yet their use, particularly in moderate to severe hypertension, is generally secondary to other agents. Diuretics also tend to deplete serum potassium, which can have serious consequences in the cardio-compromised patient.

The indirect vasodilators are probably the most extensively used agents for mild to moderate hypertension. These agents, for the most part, act on some part of the sympathetic nervous system. Propranolol, a beta adrenergic blocker, is widely used in this country to varying degrees of success. Propranolol alone, though, provides poor control of hypertension. Such therapy can also lead to various uncomfortable side effects including a prolonged reduction in cardiac output accompanied by depression, impotence, and a pronounced lethargy. Other indirect acting agents, including Guanethidine, Pargyline, Methyldopa, Reserpine, Clonidine, and the ganglionic blockers, have also displayed varying degrees of success with numerous side effects and untoward reactions.

Similarly, problems with side effects are common with long term use of drugs that act directly on the vascular smooth muscle. Diazoxide is both hyperuricemic and hyperglycemic. Nitroprusside is a powerful vasodilator but its effects are transient and the drug must be given by continuous infusion. Hydralazine is used regularly even though the incidence of untoward reactions is very high.

In all of these agents, the main problems facing the physician are efficacy and side effects. In the area of antihypertensives, even minor side effects can result in the serious problem of patient non-compliance. In terms of efficacy, the direct acting agents appear to offer the best control of the hypertensive state yet their toxicities and other limitations tend to decrease their usefulness, particularly in mild to moderate cases. It is in the interest of medical science, therefore, to develop new approaches to the treatment of hypertension.

SUMMARY OF THE INVENTION

The present invention provides a hypotensive composition comprising a peptide having the structure X-Y, Y-X, or a salt thereof, wherein X is proline or proline-proline and Y is arginine, lysine, arginine-arginine, lysine-lysine, arginine-lysine, or lysine-arginine, together with a pharmaceutically suitable diluent.

It also provides a method for alleviating hypertension in hypertensive mammals which comprises administering to the mammal an antihypertensive effective amount of a peptide having the structure X-Y, Y-X, or a salt thereof, wherein X is proline or proline-proline and Y is arginine, lysine, arginine-arginine, lysine-lysine, arginine-lysine, or lysine-arginine.

DETAILED DESCRIPTION OF THE INVENTION

This invention provides a series of 24 small peptides, two to four amino acids in length, which represent a new class of therapeutically useful antihypertensive agents. The general structure of the peptides included in the present invention can be defined as XY or YX, where X is proline (Pro) or proline-proline; and Y is arginine (Arg), lysine (Lys), arginine-arginine, lysine-lysine, arginine-lysine, or lysine-arginine. This yields the following 24 possible combinations:

| XY | YX |
|---|---|
| Pro—Arg | Arg—Pro |
| Pro—Lys | Arg—Pro—Pro |
| Pro—Arg—Arg | Lys—Pro |
| Pro—Lys—Lys | Lys—Pro—Pro |
| Pro—Arg—Lys | Arg—Arg—Pro |
| Pro—Lys—Arg | Arg—Arg—Pro—Pro |
| Pro—Pro—Lys | Lys—Lys—Pro |
| Pro—Pro—Arg—Arg | Lys—Lys—Pro—Pro |
| Pro—Pro—Lys—Lys | Arg—Lys—Pro |
| Pro—Pro—Arg—Lys | Lys—Arg—Pro |
| Pro—Pro—Lys—Arg | Lys—Arg—Pro—Pro |
| Pro—Pro—Arg | Arg—Lys—Pro—Pro |

The compositions of the present invention may be synthesized by known polypeptide synthesis methods. These peptides are then administered to the hypertensive mammal in a suitable diluent, such as normal saline, the peptide in an amount effective to reduce the mammal's blood pressure.

The present invention may be better understood by reference to the following examples.

EXAMPLE 1

Corticotropin Inhibiting Peptide (CIP) contains the following amino acid sequence, the underlined sequences of which are the sequences which are the subject of the present invention:

Human CIP (ACTH 7-38): Phe-Arg-Trp-Gly-Lys-Pro-Val-Gly-Lys-Lys-Arg-Arg-Pro-Val-Lys-Val-Tyr-Pro-Asn-Gly-Ala-Glu-Asp-Glu-Ser-Ala-Glu-Ala-Phe-Pro-Leu-Glu [M.W. 3659.68]

This CIP fragment was obtained from the Peninsula Laboratories, San Carlos, CA. When administered to dogs, this peptide resulted in dose-related hypotension.

The dog blood pressure assay was conducted according to the following method:

Mongrel dogs of either sex weighing between 6-15 kg were anesthetized by intravenous injection of sodium pentobarbital (30 mg/kg). The femoral artery and vein were cannulated for the measurement of blood pressure and the injection of drugs, respectively. Arterial blood pressure was determined with a Statham pressure transducer and was recorded on a Grass polygraph. Mean arterial pressure (MAP) was calculated for the periods before and after each peptide injection. A tracheotomy was performed to insure a patent airway for spontaneous respiration.

Hypotensive screening studies involved injecting each dog with 0.1; 0.5; 1.0; and 2.0 ug/kg. The CIP as supplied by Peninsula Laboratories was in the lyophilyzed form. Prior to injection the CIP was dissolved in saline.

Table 1 summarizes the results obtained.

TABLE 1

Dose-dependent hypotensive activity of CIP

| Dose (μg/kg) | Blood Pressure Decrease (mmHg) |
|---|---|
| 0.1 | 7 |
| 0.5 | 10 |
| 1.0 | 19 |
| 2.0 | 21 |

EXAMPLE 2

The above-described dog blood pressure assay was also used for a determination of the antihypertensive effect of the following peptides, all of which were procured from Peninsula Laboratories. For each peptide, the amino acid sequences described by the present invention are underlined:

| Peptide | Amino acid sequence |
|---|---|
| Bradykinin | Arg—Pro—Pro—Gly—Phe—Ser—Pro—Phe—Arg [M.W. 1060.24] |
| Xenopsin | pGlu—Gly—Lys—Arg—Pro—Trp—Ile—Leu [M.W. 980.32] |
| Neurotensin | pGlu—Leu—Tyr—Glu—Asn—Lys—Pro—Arg—Arg—Pro—Tyr—Ile—Leu [M.W. 1673.15] |
| Substance P | Arg—Pro—Lys—Pro—Gln—Gln—Phe—Phe—Gly—Leu—Met—NH$_2$ [M.W. 1347.80] |

The maximum decrease in blood pressure of the hypotensive effects of these peptides in dogs by the assay described above in EXAMPLE 1 is shown in Table 2. Each datapoint represents the mean of 4 replications.

TABLE 2

| Hypotensive agent | Dose (moles/kg) | Maximum Decrease in Blood Pressure (mmHg) |
|---|---|---|
| Substance P | $5 \times 10^{-10}$ | 50 |
| Bradykinin | $3 \times 10^{-9}$ | 44 |
| Neurotensin | $7 \times 10^{-10}$ | 40 |
| Xenopsin | $3 \times 10^{-9}$ | 32 |

EXAMPLE 3

The following peptides include amino acid sequences (underlined) described by the present invention:

| Peptide | Amino acid sequence |
|---|---|
| Tuftsin | Thr—Lys—Pro—Arg |
| Neurotensin (8-13) | Arg—Arg—Pro—Tyr—Ile—Leu |
| CIP fragment | Gly—Lys—Lys—Arg—Arg—Pro—Val—Lys |
| Contraceptive tetrapeptide | Thy—Pro—Arg—Lys |

When administered to a rat, each peptide exerted dose-related hypotensive effects. These results are shown in Table 3. Each datapoint represents the mean of 4 replications.

The rat blood pressure assay was conducted as follows:

Sprague-Dawley rats of both sexes, weighing between 100 and 200 grams, were anesthetized with sodium pentobarbital and the right carotid artery and jugular vein were cannulated with polyethylene tubing PE50. The hypotensive peptide was administered and blood pressure was recorded in the anesthetized rats as described above for dogs.

TABLE 3

Dose—Dependent Hypotensive Activity of Selected Peptides

| | Blood Pressure Decrease (mmHg) | | | |
|---|---|---|---|---|
| Dose (μg/kg) | Tuftsin | Neurotensin (8-13) | CIP fragment | Contraceptive tetra peptide |
| 0.1 | | 0 | | |
| 1.0 | | 13 | | |
| 3.0 | | 48 | | |
| 10.0 | | 63 | 1 | |
| 50.0 | | | 18 | |
| 100.0 | | | 35 | 2 |
| 200.0 | | | | 3 |
| 300.0 | | | 38 | |
| 500.0 | | | | 9 |
| 1000.0 | 1 | | | 13 |
| 2000.0 | | | | 15 |
| 3000.0 | 12 | | | |
| 5000.0 | 30 | | | |
| 9000.0 | 46 | | | |

EXAMPLE 4

The dipeptides proline-lysine and arginine-proline were also tested for their hypotensive action in rats. These dipeptides were synthesized by Vega Biochemicals, Tucson, AZ, and tested in the rat blood pressure assay according to the same method described above in EXAMPLE 3. The results were as follows:

| Dipeptide | Blood Pressure Change in mm Hg at dose of | | |
|---|---|---|---|
| | 1 mg/kg | 2 mg/kg | 3 mg/kg |
| L Arg—L Pro[A] | −0.8 ± 0.8 | −1.3 ± 0.8 | −13.8 ± 4.4 |
| L Pro—L Lys[B] | +0.2 ± 2.6 | −2.6 ± 1.9 | −7.0 ± 3.4 |

[A]All values are average of four replications.
[B]All values are average of five replications.

EXAMPLE 5

These dipeptides, L Arg-L Pro and L Pro-L Lys, were also tested in the rat tail artery helical strip in vitro assay. This assay is conducted according to the following method:

Male and female Sprague-Dawley rats were anesthetized with pentobarbital (50 mg/kg) before removal of the tail artery. Upon isolation the artery was placed in ice cold Krebs-Hensleit solution (KHS) which was oxygenated with 95% $O_2$, 5% $CO_2$. The vessels were cut helically and strips of approximately 1.5 cm were secured in a Sawyer-Bartleston chamber containing KHS. The development of force of the helical strips was measured with a Grass FT.03 force displacement transducer and recorded on a Grass Model 79D polygraph. Isolated tail artery helical strips were equilibrated for one hour prior to addition of any peptide. In all cases, the strips were first contracted by adding arginine vasopressin (AVP), to the bath. The peptide being studied was then added to the bath and the degree of relaxation was determined.

The pure amino acids L-proline, L-arginine, and D-arginine were included in this assay as controls.

The results were as follows:

| Dipeptide | Tension change in gm at dose of | | |
|---|---|---|---|
| | 100 mg/ml | 200 mg/ml | 500 mg/ml |
| L Arg—L Pro | −0.07 | −0.18 | −0.34 |
| L Pro—L Lys | −0.09 | −0.16 | −0.25 |
| L Pro | 0 | 0 | 0 |
| L Arg | 0 | 0 | 0 |
| D Arg | 0 | 0 | 0 |

EXAMPLE 6

Addition of lysine to the bradykinin molecule above results in the following amino acid sequence: Lys-Arg-Pro-Pro-Gly-Phe-Ser-Pro-Phe-Arg.

When tested in the rat blood pressure assay this analog was even more hypotensive than bradykinin itself.

The above examples are provided by way of illustration only, and are not to be construed as a limitation on the scope of the invention defined by the following claims.

What is claimed is:

1. A hypotensive active peptide having the L-form amino acid sequence:

| | |
|---|---|
| Pro—Lys; | Lys—Arg—Pro; |
| Pro—Arg—Arg; | Arg—Lys—Pro; |
| Pro—Lys—Lys; | Pro—Pro—Arg—Arg; |
| Pro—Arg—Lys; | Pro—Pro—Arg—Lys; |
| Pro—Lys—Arg; | Pro—Pro—Lys—Lys; |
| Pro—Pro—Arg; | Pro—Pro—Lys—Arg; |
| Pro—Pro—Lys; | Arg—Arg—Pro—Pro; |
| Lys—Pro—Pro; | Lys—Lys—Pro—Pro; |
| Lys—Lys—Pro; | Arg—Lys—Pro—Pro; or |
| | Lys—Arg—Pro—Pro, | and pharmaceutically acceptable salts thereof.

2. A hypotensive active peptide having the L-form amino acid sequence:
Pro-Lys;
Pro-Arg-Lys;
Lys-Arg-Pro; or
Lys-Arg-Pro-Pro,
and pharmaceutically acceptable salts thereof.

3. A hypotensive active peptide having an L-form amino acid sequence:

| | |
|---|---|
| Pro—Arg—Arg; | Pro—Pro—Arg—Arg; |
| Pro—Lys—Lys; | Pro—Pro—Arg—Lys; |
| Pro—Arg—Lys; | Pro—Pro—Lys—Lys; |
| Pro—Lys—Arg; | Pro—Pro—Lys—Arg; |
| Pro—Pro—Arg; | Arg—Arg—Pro—Pro; |
| Pro—Pro—Lys; | Lys—Lys—Pro—Pro; |
| Arg—Lys—Pro; | Arg—Lys—Pro—Pro; or |
| | Lys—Arg—Pro—Pro; | and pharmaceutically acceptable salts thereof.

4. The hypotensive active peptide of claim 3 which has the L-form amino acid sequence:
Pro-Arg-Lys or
Lys-Arg-Pro-Pro
and pharmaceutically acceptable salts thereof.

* * * * *